United States Patent [19]
Hogg et al.

[11] 3,936,666
[45] Feb. 3, 1976

[54] APPARATUS FOR MEASURING A PARTICLE SIZE DIVIDING ONE OF THE MASS OR PARTICLE NUMBER OF A PARTICULATE SYSTEM INTO PREDETERMINED FRACTIONS

[75] Inventors: Walter R. Hogg, Miami Lakes; Edward Neal Doty, Pompano Beach, both of Fla.

[73] Assignee: Coulter Electronics, Inc., Hialeah, Fla.

[22] Filed: Sept. 16, 1974

[21] Appl. No.: 505,970

[52] U.S. Cl. ...... 235/151.3; 324/71 CP; 235/92 PC
[51] Int. Cl.² ......................................... G01N 15/00
[58] Field of Search ......... 235/151.3, 92 PC, 92 FL; 324/71 CP; 356/39, 102

[56] References Cited
UNITED STATES PATENTS

| | | | |
|---|---|---|---|
| 3,444,463 | 5/1969 | Coulter et al. | 324/71 |
| 3,557,352 | 1/1971 | Hogg | 235/151.3 |
| 3,626,166 | 12/1971 | Berg et al. | 235/92 PC X |
| 3,657,725 | 4/1972 | Estelle et al. | 324/71 |
| 3,686,486 | 8/1972 | Coulter et al. | 324/71 X |
| 3,742,194 | 6/1973 | Caruso et al. | 235/92 PC |
| 3,783,391 | 1/1974 | Hogg et al. | 324/71 X |

Primary Examiner—Edward J Wise
Attorney, Agent, or Firm—Silverman & Cass, Ltd.

[57] ABSTRACT

A particle study apparatus which in response to passage of particles in suspension through a sensing device produces electrical pulses which are proportional in amplitude to the size of the respective particles. The apparatus includes a system for ascertaining the particle size above and below which size predetermined fractions of one of the total mass and total number of the particles in suspension are respectively included. If total mass is desired electrical quantities are accumulated in response to each electrical pulse which are proportional to the amplitudes of the electrical pulses. If total number is desired constant electrical quantities are accumulated in response to each electrical pulse. The electrical quantities are designated as being in one of two categories depending upon whether the electrical pulses producing same are greater than or less than a variable threshold. The variable threshold is varied in response to the accumulation of the electrical quantities in order to produce a desired relationship between the quantities such that the accumulated quantities are indicative of the relationship. These quantities are calibrated according to size in order to yield an output representing the dividing size of one of the mass or number of particles in the particulate system.

21 Claims, 2 Drawing Figures

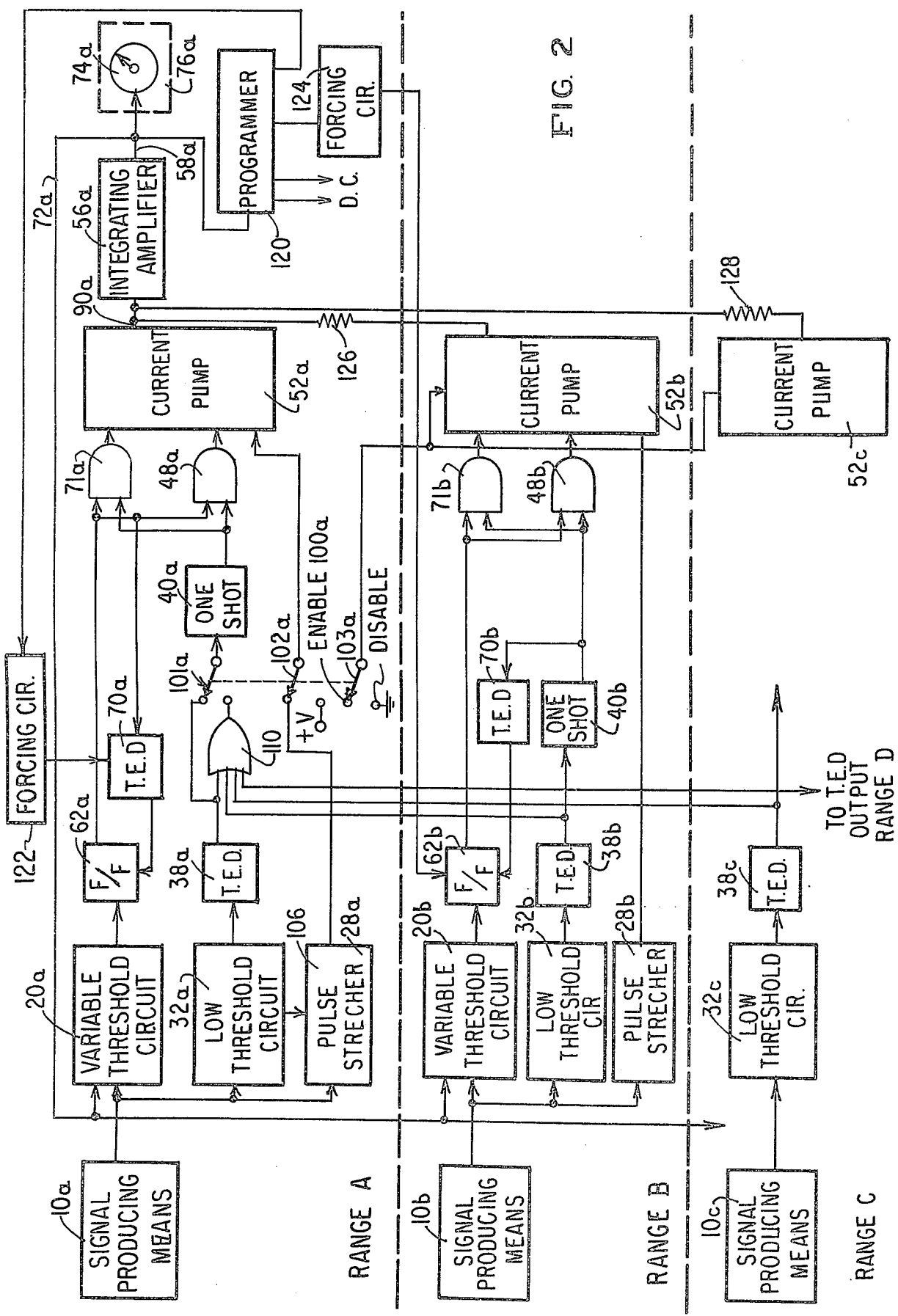

APPARATUS FOR MEASURING A PARTICLE SIZE DIVIDING ONE OF THE MASS OR PARTICLE NUMBER OF A PARTICULATE SYSTEM INTO PREDETERMINED FRACTIONS

CROSS REFERENCE TO RELATED PATENTS

This patent is related to U.S. Pat. No. 3,557,352, issued Jan. 19, 1971, which to the extent necessary, is to be considered incorporated herein by this reference.

BACKGROUND OF THE INVENTION

The invention herein relates generally to the art of studying the physical properties of particulate systems and more particularly is concerned with ascertaining accurately certain sizing information about a particulate system.

More specifically, the invention is concerned with obtaining information useful in industry and other processes where it is essential to describe the system by such highly significant statistical quantities as median size or mass as defined in the incorporated patent, and particle size which divides the number of particles in the system such that a predetermined percentage of the number of particles are smaller and/or larger than the selected size. The most useful dividing size will hereinafter be identified as the number or popululation median. That is, the size above and below which exit 50% by number of the particles in the particulate system. It is desireable to be able to ascertain this statistical information using the same equipment as previously used for ascertaining the mass median.

In the apparatus identified in U.S. Pat. No. 3,557,352 the particles in a particulate system are passed through a Coulter type of particle detector. Each particle causes a particle pulse to be developed whose amplitude is proportional to the size of the particle. As explained in greater detail in the above noted patent, size is related to mass so that the size of the particle pulse is related to the mass of the particle producing the particle pulse. The particle pulses produced by passage through the Coulter type particle detector are changed into representative electrical quantities, such as charges, which are proportional to the pulse amplitudes and hence, the respective size and mass of the particles themselves. These electrical quantities can be of a positive or a negative polarity depending on whether the particle pulse amplitude exceeds or falls below a variable threshold. The representative electrical quantities are passed to an accumulation circuit which builds up a charge that is related to the total number of charges coupled thereto, both plus and minus. The accumulating circuit will develop a signal which is related to the total charge thereon which is used to either manually adjust the threshold level of the threshold circuit, or is electrically fed back to the threshold circuit so that the positive and negative representative electrical quantities achieve a desired relationship with respect to one another. For example, the total charge accumulated will reach a point such that the threshold is adjusted to cause an equal number and amplitude of positive and negative charges to be coupled to the accumulating means. When they are equal the charge or voltage in the accumulating circuit will represent the size of particle which divides the system mass into predetermined fractions such as, for example, the mass median.

A second patent of interest to this application is U.S. Pat. No. 3,710,263 issued Jan. 9, 1973, and assigned to the same assignee as the patent which is incorporated by reference. In this patent a previous duration memory percentile responsive circuit is shown in FIG. 4 and described at columns 15 and 16. This circuit is substantially similar in configuration to a portion of the circuit shown in FIG. 6 of the incorporated patent. In the circuit shown in FIG. 4, of U.S. Pat. No. 3,710,263, pulses of varying width are coupled to the input. The circuit is operable to accumulate a representative electrical quantity, such as charge, of fixed amplitude and duration in response to each varying width pulse coupled thereto. These electrical quantities can be positive or negative depending on whether the pulse width exceeds or falls below a variable pulse width threshold. The quantities are passed to an accumulation circuit which builds up a charge related to the total number of charges received. This charge is converted to a voltage used to control the variable threshold and is a voltage representing the median duration of pulses coupled thereto. That is, there will be as many pulses greater in duration represented by the voltage as there will be pulses smaller in duration so that a voltage representative of the pulse width median is obtained.

Neither patent shows or describes apparatus capable of providing the statistical information of number median nor do they show or describe apparatus capable of providing either one of mass or number median.

SUMMARY OF THE INVENTION

In practicing this invention, an apparatus is provided which ascertains the particle size above and below which size predetermined fractions of one of the total mass and number of the system are respectively included, with the particle size being the dividing size between fractions. The apparatus includes a particle detector which produces particle pulses in response to passage of particles in suspension one by one through a sensing device. The particle pulses are proportional in amplitude to the size of the respective particles producing them. Since size is directly related to mass as explained in the above noted U.S. Pat. No. 3,557,352, the pulse amplitudes are representative of the mass of the particles producing them.

The apparatus further includes a device for generating first representative electrical quantities, such as current, which are respectively proportional to the amplitudes of the particle pulses. A second device generates second constant amplitude and duration representative electrical quantities, such as for example current, in response to the particle pulses. The electrical quantities generated will be separated into two categories on the basis of the size of the particles respectively producing the quantities. The first category comprises all quantities greater than a measuring level and the second category comprises all quantities less than the measuring level, the measuring level being calibrated to be proportional to particle size. An accumulator is provided for accumulating either all the first or second representative electrical quantities. The accumulator develops a signal which is representative of a particular relationship between the first and second categories. A device is provided for adjusting the measuring level established in order to produce a desired relationship between the first and second categories such that the accumulated representative quantities are indicative of the desired relationship between the two categories and identifies the dividing size.

In one embodiment, the mass median apparatus described in U.S. Pat. No. 3,557,352 is employed and the circuit configuration is modified via a unique switching arrangement in order to provide one or the other of the desired statistical quantities.

BRIEF DESCRIPTION OF THE DRAWINGS

FIG. 2 is a block diagram illustrating an apparatus embodying a number of ranges, each operating to respond to a different particle size range, the apparatus being adapted to ascertain the dividing size of a system for certain mass percentiles and the number median dividing size of a system.

DETAILED DESCRIPTION OF THE DRAWINGS

Figure 1:
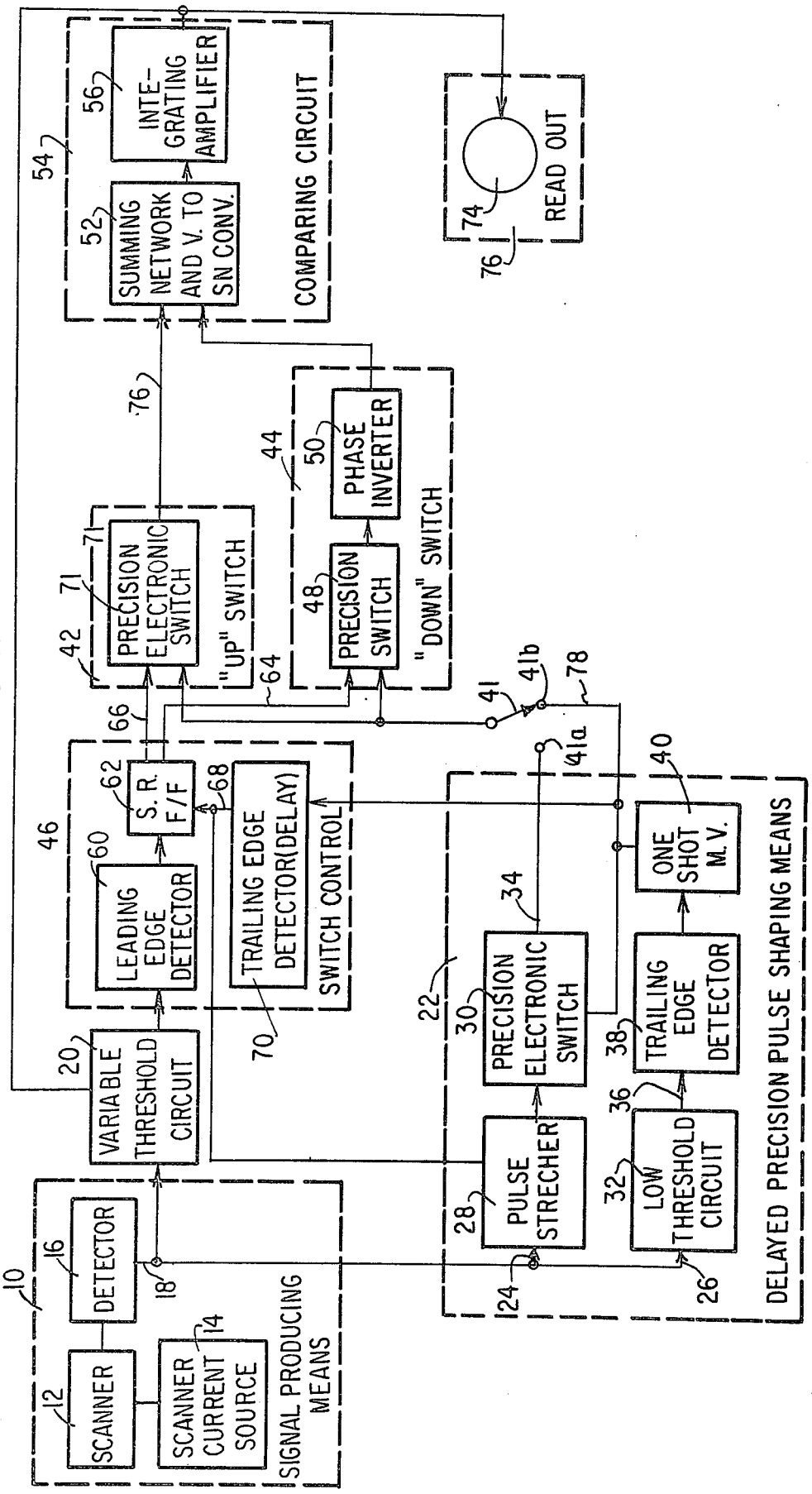
FIG. 1 is a block diagram of the combined mass median and number median apparatus of this invention.

Referring to FIG. 1 a signal producing means 10 is identified by the broken-line marks on the left and may be assumed to consist of a Coulter type particle detector. The scanner 12 comprises the Coulter type glassware and includes an aperture tube, electrodes, electrical connections, means for closing the flow of fluid, etc. For a more detailed explanation of the Coulter type particle detector reference may be made to U.S. Pat. No. 2,656,508 which discloses the principles of operation of such detectors and the basic apparatus employed. The aperture of the scanner has the usual source of current 14 which, although shown as a separate block, would customarily be included in the same housing with the amplifier and its electronics. The amplifier and associated circuitry serve to detect the signals produced in the scanner 12 and hence are referred to as detector 16. For the purposes of this application, a considerable portion of the detecting apparatus shown could be eliminated, since all that is required at the output 18 is a succession of pulses, each of which is proportional to the size of the particle which produced it. The usual threshold circuits, cathode ray osciloscope, counters and the like are not necessary, but could be convenient for the worker.

The particle pulse signals developed at 18 are applied to a variable threshold circuit 20 and to a delayed precision pulse shaping means 22, the latter being a broken line block containing a plurality of components to be described. There are two inputs into the shaping means 22, one at 24 and one at 26. The pulse stretcher 28 is a circuit which retains the amplitude of the incoming signal until a rectangular pulse of precise duration and the particular amplitude is produced. This latter effect occurs in the precision electronic switch 30, and the control for this function is obtained by means of the input 26.

The input 26 is applied to a low threshold circuit 32 set at a level which does not respond to electrical noise. This is quite close to the base line of the particle-produced pulse signal waveform, representing substantially the smallest practical particle which will be detected. Any signal which does not exceed this threshold level will not produce pulses at the output 34 of precision electronic switch 30. Any signal which does exceed this low threshold will cause a pulse at conductor 36 which will have its trailing edge deted by trailing edge detector 38. This produces a small pip or trigger pulse that triggers the one shot multivibrator 40 for a time sufficient to produce the desired duration of operation of the precision electronic switch 30. As a result, conductor 34 receives a pulse having an amplitude of the particle produced pulse and a duration of the pulse from the multivibrator 40.

As thus far described, the output at conductor 34 is a succession of current pulses of known duration and of amplitude proportional to particle size, which are coupled through a single pole two position switch 41 to one input of an up switch 42 and a down switch 44. A switch control circuit 46 is coupled between the output of variable threshold circuit 20 and a second input to up switch 42 and a down switch 44. Switch control 46 preconditions switches 42 and 44 so that all current pulses coupled from conductor 34 through switch 41 to down switch 44, which are developed as a result of particle pulses lower in amplitude than the threshold level of variable threshold circuit 20, will be passed through precision switch 48 in down switch 44; will be inverted in the phase invertor 50, and will then pass into the summing network 52 in comparing circuit 54 as a negative charge. From the summing network, the charge is applied to an integrator 56 which is a very high gain circuit, so that at conductor 58 there will be a voltage output proportional to the charge stored in the summing network 52.

If the pulse at conductor 18 is greater in amplitude than the level of the variable threshold circuit 20, a pulse will be developed by variable threshold circuit 20 which is coupled to a leading edge detector 60 in switch control 46. Leading edge detector 60 will produce a pulse in response to the leading edge of the pulse from variable threshold circuit 20 which is coupled to the set input of a set-reset flip-flop 62. The set-reset flip-flop 62 is normally in a reset state so that the output coupled to down switch 44 via conductor 64 enables down switch 44 and the output coupled to up switch 42 via conductor 66 disables up switch 42. The trigger pulse applied to the set input of flip-flop 62 causes flip-flop 62 to change states coupling an enable signal to up switch 42 via conductor 66 and a disable signal to down switch 44 via conductor 64. This allows the pulse developed by precision electronic switch 30, whose amplitude is proportional to the particle pulse amplitude developed at conductor 18, to be coupled via switch 41 to the input of precision electronic switch 71 in up switch 42, and through switch 71 into the summing network 52 of comparing circuit 54 as a positive charge. From the summing network 52 the charge is applied to integrator 56.

Flip-flop 62 will remain in this state until a pulse is applied to its reset input via conductor 68. The reset pulse is generated by detecting the trailing edge of the pulse developed by one shot 40 by means of a trailing edge detector 70. This reset delay allows the charge to be first accumulated before the circuit is reset. Trailing edge detector 70 also couples its pulse to pulse stretcher 28 for resetting the pulse stretcher after the positive or negative charge is accumulated.

In this manner the output of summing network 52 and the input of integrating amplifier 56 will be continuously developing thereat the algebraic sum of charges applied thereto from the two separate paths. Since there is always a finite output of substantial voltage at 58, due to the high gain of the integrating amplifier 56, it can be used to change the level of the variable threshold circuit 20 automatically through the feedback connection 72 and is measured in a suitable voltmeter 74 in readout means 76. When a certain percentage of the particulate system has been passed through the detector, a state of equilibrium will be reached by the voltage at the integrating amplifier 56. The signal coupled via conductor 72 to variable threshold circuit 20 will adjust the threshold such that the particle pulses will cause an equal number and amplitude of positive and negative charges to be accumulated so that the total charge accumulated and the voltage at output 58 will reach this equilibrium state. That is, the number and amplitude of positive and negative charges will cancel yielding a predetermined charge level over a period of time.

The charge developed at integrating amplifier 56 and the voltage developed at conductor 58 is related to the particulate mass of particles larger and smaller than the measuring level respectively because the variable in this circuit is the charge amplitude or magnitude which is varied in accordance with the size of the particle pulses. As the particle pulse size varies in accordance with the particle size, which is related to volume, the charge accumulated and therefore the feedback voltage at conductor 58 will be related to, and is preferably proportional to the size and the mass of the particles in the particulate system. The apparatus previously described is most often used to determine mass median as defined in the incorporated U.S. Pat. No. 3,557,352, however, it should be understood that as explained in that patent the apparatus can be used to find the 25th, 50th or 75th mass percentile or any desired mass percentile dividing size.

The signals appearing at conductor 18 of the signal producing means 10 are electrical pulses whose amplitudes are respectively proportional to the sizes of the particles that produced the same. The duration of each signal is proportional to the time that the particle required in passing through the effective scanning ambit of the scanner 12. A characteristic of these signals that is accurately representative of the size of particles is their amplitude and hence these signal are all changed into signals having the identical duration. The factor of duration thus drops out of the determination to be made. Once having achieved these precision signals, they are required to be converted into representative electrical quantities such as charges, since non-coexistant voltages cannot be added or subtracted. The preferred manner of shaping and switching the signals is in voltage form because this is the simplest way of doing it electronically and because the charge on a capacitor is proportional to its terminal voltage. Accordingly, when the signals appear at the output terminals of precision electronic switch 72 and phase invertor 50 they are preferably voltages.

As noted previously, it is most desirable to be able to determine fractional number distribution and particularly number median as compared to mass percentile distribution and mass median. This can be implemented using the same apparatus previously described by the addition of the previously noted switch 41 and a conductor 78 coupling the output of one shot 40 to a second contact of switch 41. With the movable arm of switch 41 in contact with terminal 41a, the apparatus operates as a mass percentile determining circuit. With the movable arm in contact with terminal 41b, the apparatus operates as a fractional number determining circuit. With the arm of switch 41 connected to terminal 41b the output of precision electronic switch 30 is no longer connected to an input of precision electronic switches 48 and 71 in down switch 44 and up switch 42 respectively. These switch inputs are now connected via switch 41 and terminal 41b to the output of one shot 40 so that the pulses passing through switches 42 and 44 and summed in summing network 52 will be equal duration and amplitude. With variable amplitude pulses replaced by constant amplitude pulses the variation in output due to mass is eliminated and the variation will be solely dependent upon the number of particle pulses. As the system will reach an equilibrium as a result of the feedback via conductor 72 to variable threshold circuit 20, the equilibrium will be at a point identifying a percentile division between numbers of particles. The percentile division will be determined by the operation of summing network 52 and in the preferred embodiment is 50 percent so that the accumulated charges both positive and negative will be equal in response to each and every pulse when an equilibrium state is reached. As the signal on conductor 72 and output 58 is a voltage, and as this voltage is related to the input voltage which is of course related to size, the voltage at conductor 72 and output 58 may be calibrated and related to size so that the reading at voltmeter 74 will be representative of a size above which and below which lie a predetermined fraction of the total number of particles in the system. In the preferred embodiment the voltage will represent a size above and below which lie 50% of the total number of particles in the system which is the number median.

Referring now to FIG. 2 there is shown an apparatus which may be used with a particulate system having a very wide range of particulate distribution. In the apparatus of FIG. 2 the signal producing means comprise several structures which may be of the Coulter type, these being designated 10a, 10b, 10c, and so on in order to designate the signal sources for channels or ranges a, b, c or d. Although signal producing means 10a, b, c, d, etc. may be separate devices, they may also be a single device capable of detecting particles over extremely wide size range with separate, serially-connected amplifiers for amplifying the detected signals with the output of each serially-connected amplifier coupled to a different one of the identified ranges in order to detect pulses only within a specified range of sizes. Each one of the ranges is substantially identical in structure to every other range and is also substantially identical to the structure shown in FIG. 1. Components in FIG. 2 which are identical to and/or perform the same function as components in FIG. 1 wil be identified by the identical number and further explanation of the operation of those common portions will not be provided except where a specific embodiment is provided in place of a generalized structure shown in FIG. 1. Referring more specifically to Range A in FIG. 2, AND gate 48a is the specific embodiment employed for precision switch 48 of FIG. 1, and AND gate 71a is the specific embodiment employed for precision switch 71. A programmable current pump 52a replaces summing network and voltage to charge convertor 52 in FIG. 1. Current pump 52a will develop a charging current pulse at conductor 90 which is positive if AND gate 72a is on and negative if AND gate 48a is on. The amplitude of the current pulse developed at conductor 90a will vary in accordance with the amplitude of the pulse developed at, and coupled from pulse stretcher 28a to current pump 52a via pole 102a of switch 100a.

Switch 100a is a 3-pole, 2-position switch in the embodiment shown consisting of poles 101a, 102a, and 103a. With switch 100a in the position shown the apparatus operates in the manner as described with respect to the apparatus shown in FIG. 9 of the incorporated patent with the exception that certain components are replaced by a specific embodiment identified above and with the further exception that pulse stretcher 28a is reset via a pulse on a conductor 106 from low threshold circuit 32a at the beginning of each newly received particle pulse, rather than a predetermined period of time after the end of each particle pulse, in order to eliminate the possibility of noise or other extraneous signals adding to the amplitude of the pulse coupled through pulse stretcher 28a.

In FIG. 2, the output of trailing edge detectors 38a, b, c, and d are coupled to the inputs of OR gate 110 in addition to being coupled to their associated one shots 40a, b, c or d. The output of OR gate 110 is coupled to one terminal of pole 101a in switch 100a. With switch 100a moved to its alternate position, the output of OR gate 110 will be coupled via pole 101a to the input of one shot 40a. In this alternate position, switch 110a will also couple a constant reference voltage to the amplitude or variable input of programmable current pump 52a via pole 102a, and a disable signal to the programmable current pumps 52b, c, and d respectively in ranges b, c, and d via pole 103a. With switch 100a in this alternate position, the entire apparatus will now operate in the same manner as described with respect to the apparatus of FIG. 1 when the movable arm switch 41 was coupled to terminal 41b. That is, the apparatus will now measure the median size above and below which lie 50% of the total number of particles in the system.

In operation, each particle pulse developed by signal producing means 10a, b, c, or d in response to each and every particle in the system will produce a one-shot pulse at the respective trailing edge detector 38a, b, c or d of the appropriate range. These trigger pulses are OR'd together via OR gate 110 so that each of them will generate a trigger pulse at the output of OR gate 110 which is coupled to one-shot 40a. In this way, one-shot 40a will respond and develop a pulse of constant duration, just as one-shot 40 in FIG. 1, in response to each and every particle and particle pulse which exceeds any of the low thresholds in the entire system. In the circuit shown in FIG. 1, the amplitude of the charges accumulated was fixed at an amplitude determined by the output level of one-shot 40. It has been found more desirable to employ a constant reference for this purpose rather than the output of a one-shot which may vary more widely due to variations in ambient conditions. For this reason, the input to precision switches 48 and 72 in FIG. 1, which is coupled via switch 41 and contact 41b from one-shot 40, is replaced by a fixed reference voltage coupled to programmable current pump 52a via pole 102a of switch 100. Range A operates in the manner described with respect to FIG. 1 to accumulate charges at the input to integrating amplifier 56a and a voltage at output 58a. The voltage at output 58a will be fed back to variable threshold circuit 20a to adjust the threshold such that an equilibrium state will be reached, the equilibrium state producing a voltage at 50a representing the number median.

It is assumed for purposes of this discussion that it is desired to determine the number median which is provided by Range A, Ranges B, C and D providing other potentially desired percentiles. As can be seen by reference to FIG. 2, outputs of trailing edge detectors 32b, c, and d remain connected to their associated one-shots 40b, c, and d, so that the individual channels would continue to operate as previously to determine percentile mass distribution. The simultaneous accumulation of this information for only certain ranges would yield only partial and possibly even erroneous data. In order to eliminate this problem, a disable signal is coupled to programmable current pumps b, c, and d in channels b, c, and d via movable arm 103 of switch 100a when switch 100a is in the alternate position and number median is being determined.

It will be appreciated that considerable variation is capable of being made in the details of this invention without departing from the spirit or scope of the invention as defined in the appended claims.

What is desired to secure by Letters Patent of the United States is:

1. An apparatus for ascertaining that particle size above and below which size predetermined fractions of one of the total mass and number of the system are respectively included, said particle size being the dividing size between fractions, which comprises:
   A. signal producing means including:
      i. means for moving a representative sample of a particulate system suspended in a fluid medium relative to a sensing device responsive to movement of individual particles to produce electrical changes in said sensing means proportional to the respective sizes of particles; and
      ii. means for producing electrical pulses as a result of such changes, the respective electrical pulses being proportional in amplitude to the size of the respective particles producing the changes;
   B. means for generating first representative electrical quantities respectively proportional to the amplitude of said electrical pulses;
   C. means for generating second constant representative electrical quantities in response to said electrical pulses;
   D. means for separating said representative electrical quantities into two categories on the basis of the size of the particles respectively producing the same, the first category comprising all quantities greater than a measuring level, and the second category comprising all quantities less than the measuring level, said measuring level being calibrated to be proportional to particle size;
   E. means for accumulating one of said first and second representative electrical quantities;
   F. means for adjusting the measuring level to produce a desired relationship between categories such that accumulated representative quantities are indicative of said relationship and identifies said dividing size.

2. The apparatus of claim 1 wherein said means for adjusting the measuring level comprise feedback circuit means coupling said accumulating mean to said separating means.

3. The apparatus of claim 1 wherein said separating means includes comparison means operative to establish a variable threshold level varying in accordance with said accumulated electrical quantities, and further operative to separate said representative electrical quantities into said first category in response to electrical pulses greater than said threshold and into said second category in response to electrical pulses less than said threshold.

4. The apparatus of claim 1 wherein said accumulating means includes means for summing said representative electrical quantities.

5. The apparatus of claim 4 wherein said summing means includes integrator means for developing an integration signal in response to said representative electrical quantities coupled thereto, said integration signal calibrated to identify said dividing size.

6. The apparatus of claim 1 wherein said first generating means includes circuit means operative in response to said electrical pulses to produce electrical quantities having a fixed duration and variable amplitude which varies in accordance with said pulse amplitudes.

7. The apparatus of claim 6 wherein said representative electrical quantities are currents.

8. The apparatus of claim 7 wherein said first category of currents are of one polarity and said second are of another polarity.

9. The apparatus of claim 1 wherein said second generating means includes circuit means operative in response to said electrical pulses to produce electrical quantities having a fixed amplitude and duration.

10. The apparatus of claim 9 wherein said representative electrical quantities are currents.

11. The apparatus of claim 10 wherein said first category of currents are of one polarity and said second are of another polarity.

12. The apparatus of claim 1 wherein said first and second generating means include first circuit means operative in response to said electrical pulses to produce first pulses having fixed duration and, second circuit means operative in response to said electrical pulses to produce first electrical signals having an amplitude which varies in accordance with said electrical pulse amplitudes, current generation means, means for selectively coupling said first circuit means to said current generation means and both said first and second circuit means to said current generation means, said current generation means operative in response to said first pulses being coupled thereto to develop currents of fixed amplitude and duration and operative in response to said first pulses and first electrical signals coupled thereto to develop currents of fixed duration and variable amplitude, said current generation means being further coupled to said separating means and operative in response to separation into said first category to develop said currents having one polarity and operative in response to separation into said second category to develop said currents having an opposite polarity.

13. The apparatus of claim 12 wherein said selective coupling means includes switch means operative in a first position to couple a reference potential to said current generation means and operative in a second position to couple said second circuit means to said current generation means.

14. In a particle study apparatus wherein electrical pulses are produced in response to passage of particles in suspension through a sensing device, and wherein the electrical pulses are proportional in amplitude to the size and therefore mass of the respective particles, a system for ascertaining that particle size above and below which size predetermined fractions of one the total mass and number of the particles are respectively included, said particle size being the dividing size between fractions, which comprises:

A. first means for generating first representative electrical quantities in response to said electrical pulses respectively proportional to the amplitudes of said electrical pulses whereby said quantities are mass related;

B. second means for generating second constant representative electrical quantities in response to said electrical pulses;

C. selection means for selecting one of the said first and second means;

D. means for separating said representative electrical quantities into two categories on the basis of the size of the particles producing the same, the first category comprising all quantities greater than a measuring level and the second category comprising all quantities less than the measuring level, said measuring level being calibrated to be related to particle size;

E. means for accumulating the selected one of said first and second representative electrical quantities;

F. means for adjusting the measuring level to produce a desired relationship between categories such that said accumulated representative quantities are indicative of said relationship and defines said dividing size.

15. The apparatus of claim 14 wherein said second generating means include, first circuit means operative in response to said electrical pulses to produce first pulses having fixed duration, said first generating means include said first circuit means and second circuit means operative in response to said electrical pulses to produce first electrical signals having amplitudes which vary in accordance with said pulse amplitudes.

16. The apparatus of claim 15 wherein said first and second generating means include signal generating means coupled to said first circuit means and to said second circuit means through said selection means, said selection means being operative to a first position for inhibiting passage of said first electrical signals to said signal generating means whereby said signal generating means develops said second electrical quantities, and to a second position for allowing passage of said first electrical signals whereby said signal generating means develops said first electrical quantities.

17. The apparatus of claim 16 wherein said selection means is coupled to a reference signal said selection means being operative in said first position to couple said reference signal to said signal generating means.

18. The apparatus of claim 17 wherein said signal generating means is a programmable current source and said first and second electrical quantities are currents.

19. The apparatus of claim 16 wherein said signal generating means is coupled to said separating means and operative in response to separation into said first category to develop said electrical quantities to polarity and operative in response to separation into said second category to develop said electrical quantities having opposite polarity.

20. The apparatus of claim 19 wherein said signal generating means is a programmable current source and said first and second electrical quantities are currents.

21. The apparatus of claim 16 wherein said selection means include a switch operable at least between a first and second position.

* * * * *

UNITED STATES PATENT AND TRADEMARK OFFICE
CERTIFICATE OF CORRECTION

PATENT NO. : 3,936,666
DATED : February 3, 1976
INVENTOR(S) : Walter R. Hogg and Edward Neal Doty It is certified that error appears in the above–identified patent and that said Letters Patent are hereby corrected as shown below:

Column 1, line 27, change "popululation" to -- population --

Column 3, line 63, change "deted" to -- detected --.

Column 6, line 45, change "wil" to -- will --.

Column 9, line 61, insert -- of -- after "one".

Column 7, line 17, change "110a" to -- 100a --;

line 35, between "each" and "of" insert -- one --.

Column 8, lines 32-33, change "amplitude" to -- amplitudes --.

Column 10, line 56, change "to" second occurrence to -- of one --

Signed and Sealed this

Fifteenth Day of February 1977

[SEAL]

*Attest:*

RUTH C. MASON
*Attesting Officer*

C. MARSHALL DANN
*Commissioner of Patents and Trademarks*